United States Patent
Tsuyuki et al.

(10) Patent No.: US 10,205,888 B2
(45) Date of Patent: Feb. 12, 2019

(54) ENDOSCOPE SYSTEM

(71) Applicant: OLYMPUS CORPORATION, Hachioji-shi, Tokyo (JP)

(72) Inventors: Hiroshi Tsuyuki, Tokyo (JP); Mitsujiro Konno, Tokyo (JP); Akikazu Yachi, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 169 days.

(21) Appl. No.: 15/457,654

(22) Filed: Mar. 13, 2017

(65) Prior Publication Data

US 2017/0187943 A1    Jun. 29, 2017

Related U.S. Application Data

(63) Continuation of application No. PCT/JP2015/075606, filed on Sep. 9, 2015.

(30) Foreign Application Priority Data

Sep. 18, 2014 (JP) ................................ 2014-190167

(51) Int. Cl.
H04N 5/235    (2006.01)
A61B 1/04     (2006.01)
(Continued)

(52) U.S. Cl.
CPC ....... *H04N 5/2354* (2013.01); *A61B 1/00009* (2013.01); *A61B 1/00045* (2013.01);
(Continued)

(58) Field of Classification Search
CPC ... A61B 1/00; A61B 1/00009; A61B 1/00045; A61B 1/04; A61B 1/06; G02B 23/04;
(Continued)

(56) References Cited

U.S. PATENT DOCUMENTS 8,948,468 B2 * 2/2015 Steinberg ............... H04N 5/232
345/473
2013/0235174 A1 9/2013 Namii
(Continued)

FOREIGN PATENT DOCUMENTS

EP    2668891 A1    12/2013
EP    2868254 A1    5/2015
(Continued)

OTHER PUBLICATIONS

International Search Report (ISR) and Written Opinion dated Nov. 24, 2015 issued in International Application No. PCT/JP2015/075606.

*Primary Examiner* — Tung T Vo
(74) *Attorney, Agent, or Firm* — Holtz, Holtz & Volek PC

(57) ABSTRACT

An endoscope system includes: a generating means generating a compositing mask that serves as compositing ratios of the corresponding pixels between a pair of images acquired by simultaneously imaging two optical images having different focus positions, into which a subject image is divided on the basis of the ratios of contrasts; a correcting means subjecting compositing masks generated for pairs of images acquired in time series, to weighted averaging for respective pixels, thus generating a corrected mask; and an compositing means compositing the two images according to the corrected mask. The correcting means subjects the compositing masks to weighted averaging by performing weighting such that the percentage of the past compositing masks is higher at pixels constituting a static area and an area having contrast lower than a threshold than at pixels constituting a moving-object area or an area having contrast equal to or higher than the threshold.

12 Claims, 13 Drawing Sheets

(51) Int. Cl.
| | |
|---|---|
| *H04N 5/232* | (2006.01) |
| *A61B 1/00* | (2006.01) |
| *A61B 1/06* | (2006.01) |
| *G02B 5/30* | (2006.01) |
| *G02B 23/04* | (2006.01) |
| *G02B 23/24* | (2006.01) |
| *G02B 27/00* | (2006.01) |
| *G02B 27/28* | (2006.01) |
| *H04N 5/225* | (2006.01) |
| *H04N 5/265* | (2006.01) |
| *H04N 5/243* | (2006.01) |
| *H04N 9/04* | (2006.01) |

(52) U.S. Cl.
CPC ............ *A61B 1/00188* (2013.01); *A61B 1/04* (2013.01); *A61B 1/06* (2013.01); *G02B 5/3083* (2013.01); *G02B 23/04* (2013.01); *G02B 23/2423* (2013.01); *G02B 23/2453* (2013.01); *G02B 23/2461* (2013.01); *G02B 23/2469* (2013.01); *G02B 23/2484* (2013.01); *G02B 27/0075* (2013.01); *G02B 27/283* (2013.01); *G02B 27/286* (2013.01); *H04N 5/2256* (2013.01); *H04N 5/232* (2013.01); *H04N 5/2351* (2013.01); *H04N 5/243* (2013.01); *H04N 5/265* (2013.01); *H04N 9/045* (2013.01); *H04N 2005/2255* (2013.01)

(58) Field of Classification Search
CPC .......................... G02B 23/24; G02B 23/2453; G02B 23/2461; G02B 27/0075; G02B 27/286; G02B 5/3083; H04N 5/225; H04N 5/2256; H04N 5/232; H04N 5/235; H04N 5/2354; H04N 5/265
USPC .......................................................... 348/45
See application file for complete search history.

(56) References Cited

U.S. PATENT DOCUMENTS

| | | | |
|---|---|---|---|
| 2013/0271587 | A1 | 10/2013 | Tsuyuki |
| 2014/0176692 | A1 | 6/2014 | Tsuyuki et al. |
| 2014/0198194 | A1 | 7/2014 | Suga et al. |
| 2015/0002646 | A1 | 1/2015 | Namii |
| 2015/0073209 | A1 | 3/2015 | Ikeda |
| 2015/0358525 | A1* | 12/2015 | Lord .................. G06F 17/30244 358/473 |
| 2016/0345834 | A1* | 12/2016 | Hasan ................ A61K 49/0058 |
| 2018/0167542 | A1* | 6/2018 | Minden ................ H04N 5/2355 |

FOREIGN PATENT DOCUMENTS

| | | |
|---|---|---|
| EP | 2891448 A1 | 7/2015 |
| JP | 09116807 A | 5/1997 |
| JP | 2004313523 A | 11/2004 |
| JP | 2010187207 A | 8/2010 |
| JP | 2011245019 A | 12/2011 |
| JP | 2013244104 A | 12/2013 |
| JP | 5393926 B2 | 1/2014 |
| WO | 2013061819 A1 | 5/2013 |
| WO | 2014002740 A1 | 1/2014 |
| WO | 2014034339 A1 | 3/2014 |

\* cited by examiner

ENDOSCOPE SYSTEM

CROSS-REFERENCE TO RELATED APPLICATIONS

This is a continuation of International Application PCT/JP2015/075606 which is hereby incorporated by reference herein in its entirety.

This application is based on Japanese Patent Application No. 2014-190167, the contents of which are incorporated herein by reference.

TECHNICAL FIELD

The present invention relates to an endoscope system, and, in particular, to an endoscope system with extended depth of field.

BACKGROUND ART

In general, it is known that, in devices having an image acquisition element, such as endoscope systems, the depth of field is narrowed as the number of pixels in the image acquisition element becomes higher. Specifically, in the image acquisition element, when the pixel pitch (the horizontal and vertical size of one pixel) is reduced in order to increase the number of pixels, the permissible circle of confusion is accordingly reduced, and thus the depth of field of an image-acquisition device is narrowed.

Thus, there is a known endoscope in which one optical image from an objective lens is divided into two optical images having different focus positions by a polarizing beam splitter, one optical image is made to pass via a λ/4 wavelength plate and a mirror, the other optical image is made to pass via a mirror, the optical images are imaged on an image acquisition element, and the two images are composited, thereby acquiring an image in which the depth is extended (for example, see PTL 1 and PTL 2).

More specifically, PTL 1 and PTL 2 describe that a polarizing beam splitter is used as an optical-path dividing element, a depolarizing plate or a λ/4 wavelength plate is provided to suppress a luminance loss, two images are imaged on one image acquisition element to achieve a reduction in size, and a difference between the two images is corrected when the two images are composited. In particular, PTL 1 describes that the depolarizing plate is disposed between the polarizing beam splitter and the objective lens to convert light in the polarized state entering the polarizing beam splitter into circularly polarized light, thus achieving uniform polarized-light separation.

Furthermore, when there is a difference in luminance between two images, that is, far and near images, to be composited, luminance unevenness is caused in a spatial direction or in a temporal direction in the image obtained after compositing; therefore, in order to resolve this, PTL 3 describes that a subject is subjected to matching in the temporal direction to smooth the image signal, thereby suppressing luminance unevenness in the composited image.

CITATION LIST

Patent Literature

{PTL 1} Japanese Unexamined Patent Application, Publication No. 2013-244104
{PTL 2} Publication of Japanese Patent No. 5393926
{PTL 3} Japanese Unexamined Patent Application, Publication No. 2010-187207

SUMMARY OF INVENTION

Solution to Problem

According to one aspect, the present invention provides an endoscope system including: an objective optical system that is provided at a distal end of an insertion portion and that obtains a subject image of a subject irradiated with illumination light from a light source; an optical-path dividing means that divides the subject image into two optical images having different focus positions; an image acquisition element that simultaneously images the two optical images having different focus positions to acquire a pair of images; a contrast calculating means that calculates contrasts, for respective pixels, of the pair of images acquired by the image acquisition element; a mask generating means that generates a compositing mask that serves as compositing ratios of the corresponding pixels between the pair of images on the basis of the ratios of the contrasts calculated by the contrast calculating means; a mask correcting means that generates a corrected mask by applying, for the respective pixels, weighted averaging to a plurality of compositing masks that are generated in time series by the mask generating means for a plurality of pairs of images that are acquired in time series by the image acquisition element; and an image compositing means that composites the two images according to the corrected mask generated by the mask correcting means, wherein the mask correcting means applies weighted averaging to the plurality of compositing masks by performing weighting such that the percentage of the past compositing masks is higher at pixels that constitute a static area and an area having contrast lower than a predetermined threshold, in the pair of images, than at pixels that constitute a moving-object area or an area having contrast equal to or higher than the predetermined threshold, in the pair of images.

DESCRIPTION OF EMBODIMENTS

An embodiment of the present invention will be described below with reference to the drawings.

Figure 1:
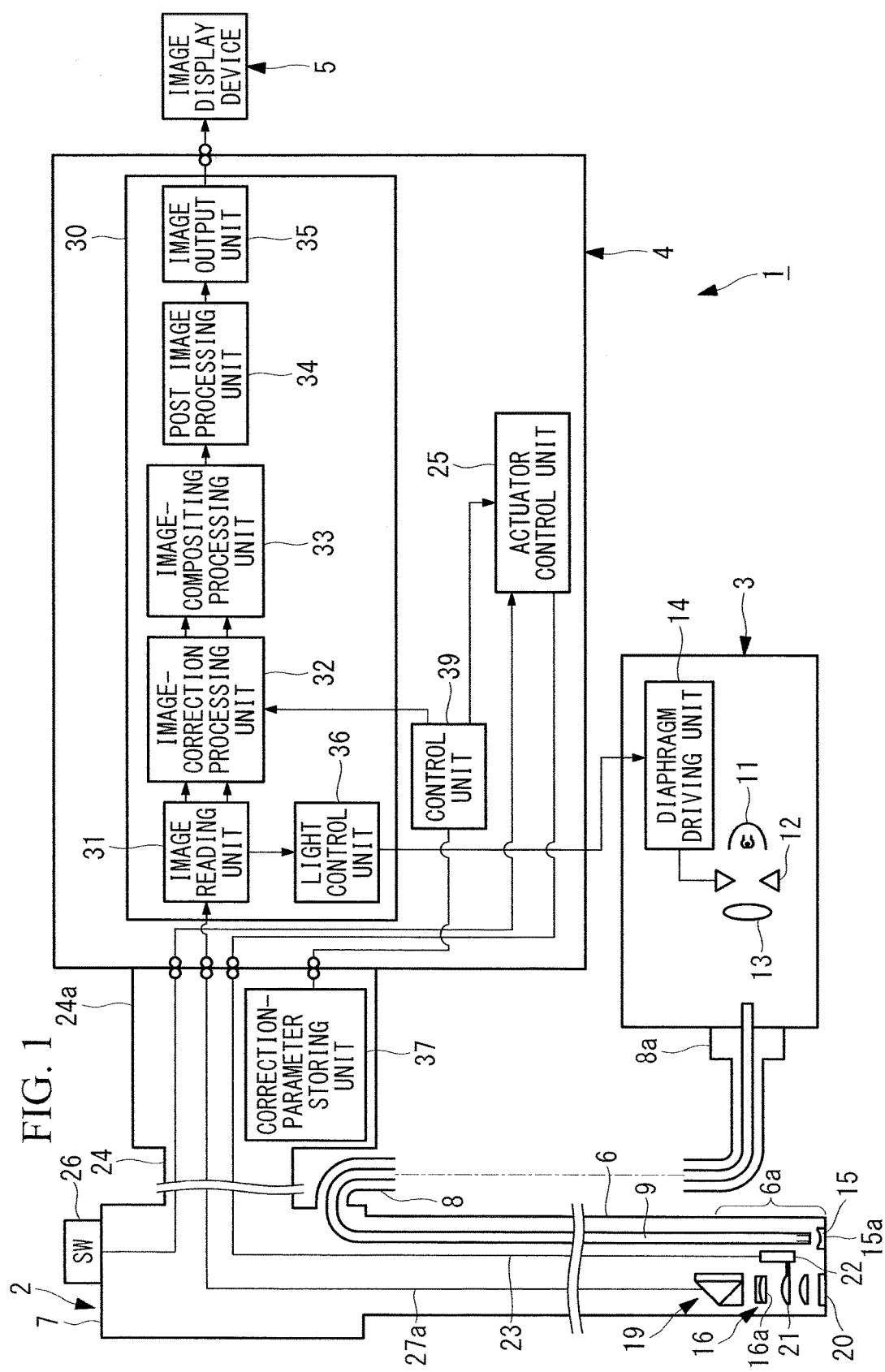
FIG. 1 is a view showing, in outline, the configuration of an endoscope system according to an embodiment of the present invention.

As shown in FIG. 1, an endoscope system 1 of the embodiment of the present invention includes: an endoscope 2; a light source device 3 that supplies illumination light to the endoscope 2; a processor device 4 that subjects an image signal obtained by an image acquisition element provided in the endoscope 2 to image processing; and an image display device 5 that displays, as an endoscope image, the image signal that has been subjected to predetermined image processing by the processor device 4.

The endoscope 2 has: an elongated insertion portion 6 that is inserted into a body to be examined; an operating portion 7 that is provided at a rear end of the insertion portion 6; and a first cable 8 that extends from the operating portion 7. A light guide 9 for transmitting illumination light is inserted through the first cable 8. An illumination lens 15 that spreads illumination light emitted from the light guide 9, an objective optical system 16 that obtains a subject image, and an image acquisition unit 19 that acquires the subject image are provided in a distal-end portion 6a of the insertion portion 6 of the endoscope 2. A light-guide connector 8a provided at an end portion of the first cable 8 is detachably connected to the light source device 3 such that a rear-end portion of the light guide 9, which is inserted through the first cable 8, serves as an entrance end of the illumination light.

The light source device 3 includes, as a light source, a lamp 11, e.g., a xenon lamp or the like. Note that the light source is not limited to the lamp 11, such as a xenon lamp, and a light-emitting diode (hereinafter, referred to as "LED") may be used. The passing light level of the white light produced in the lamp 11 is adjusted by a diaphragm 12, and the white light is then condensed by a condenser lens 13 and is incident on (supplied to) an entrance-end surface of the light guide 9. Note that the degree of opening of the diaphragm 12 can be changed by a diaphragm driving unit 14.

The light guide 9 guides illumination light entering the entrance end (rear end) thereof from the light source device 3 toward the distal-end portion 6a of the insertion portion 6. The illumination light guided to the distal-end portion 6a is spread out from an exit end (distal end) of the light guide 9 by the illumination lens 15, which is disposed on a distal-end surface of the distal-end portion 6a, and is emitted via an illumination window 15a, thus illuminating an observation target site in the body to be examined.

Light from the observation target site illuminated with the illumination light is collected by the objective optical system 16, which is mounted on an observation window 20 that is provided adjacent to the illumination window 15a on the distal-end portion 6a.

The objective optical system 16 is provided with: an optical element group 16a that is composed of a plurality of optical elements; a focus lens 21 that serves as a focus switching mechanism so as to selectively focus on two observation areas for distant observation and close observation; and an actuator 22 that drives the focus lens 21.

The image acquisition unit 19 is provided closer to a rear-end portion of the insertion portion 6 than the objective optical system 16 is and is provided with: a polarizing beam splitter 18 (optical-path dividing means) that divides a subject image into two optical images having different focus positions; and an image acquisition element 17 that images the two optical images to acquire two images.

Figure 2:
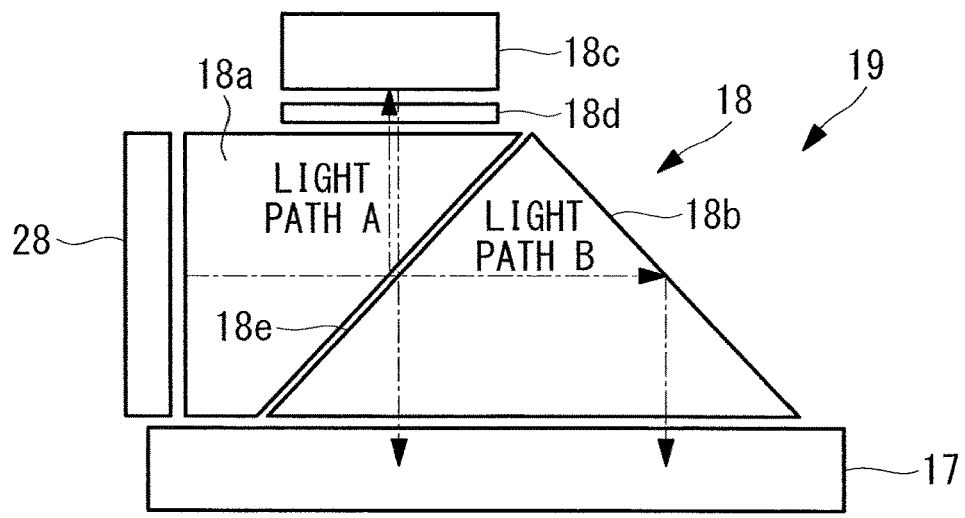
FIG. 2 is a view showing, in outline, the configuration of an image acquisition unit used in the endoscope system according to the embodiment of the present invention.

As shown in FIG. 2, the polarizing beam splitter 18 is provided with a depolarizing plate 28, a first prism 18a, a second prism 18b, a mirror 18c, and a λ/4 wavelength plate 18d.

A λ/4 wavelength plate is used as the depolarizing plate 28. If a general depolarizing plate (for producing non-polarized light through scrambling) is used in order to change the polarized state to a non-polarized state, because the size thereof is too large, and the structure thereof is complicated, the depolarizing plate is not suitable for being disposed in the distal end of the endoscope. Thus, a λ/4 wavelength plate is used as the depolarizing plate 28, thereby making it possible to convert polarized light entering the polarizing beam splitter 18 into substantially circularly polarized light and to achieve intensity uniformity.

Usually, a λ/4 wavelength plate needs to be considered at zero order, and, for example, when a wavelength plate using a crystal is used to give a ¼λ phase difference at a design wavelength of 550 nm, it is necessary to reduce the thickness of the crystal to about 15 μm. However, it is impractical to directly handle such an ultrathin filter. For the purpose of increasing the plate thickness to a practical level, a multiple-order wavelength plate is designed so as to obtain a predetermined phase difference at higher order. For example, when a phase difference of 2.5 wavelengths is produced at the wavelength of 550 nm, the plate thickness can be increased to about 150 μm if a crystal is used.

The phase difference of 2.5 wavelengths can be considered as effectively a phase difference of 0.25 wavelengths (=¼). However, with the increased plate thickness, an unignorable phase-difference shift is caused even by a slight wavelength shift or an oblique incident light beam; therefore, an image-compositing processing unit 33, to be described later, appropriately sets compositing ratios (mask) that are used to composite a pair of images, thereby making it possible to generate a good image having less luminance unevenness.

The first prism 18a and the second prism 18b both have beam splitting surfaces that are inclined at an angle of 45 degrees with respect to the optical axis. The beam splitting surface of the first prism 18a is provided with a polarized-light separating film 18e. Then, the first prism 18a and the second prism 18b constitute the polarizing beam splitter 18 by bringing their beam splitting surfaces into contact, with the polarized-light separating film 18e therebetween. Furthermore, the mirror 18c is provided in the vicinity of an end surface of the first prism 18a via the $\lambda/4$ wavelength plate 18d, and the image acquisition element 17 is attached to an end surface of the second prism 18b. Note that the $\lambda/4$ wavelength plate 18d has inverse dispersion properties.

By making the $\lambda/4$ wavelength plate 18d have the inverse dispersion properties, it is possible to provide an endoscope in which a fluctuation in the extinction ratio is reduced in visible wavelength bands, thus suppressing the luminance unevenness.

The reason is as follows. Specifically, it is preferred that two images obtained through polarized-light separation at the polarizing beam splitter 18 do not have a large difference in luminance intensity. In a returning light path, polarized light passing through the $\lambda/4$ wavelength plate and the mirror is rotated in direction by 90 degrees, thus becoming P-polarized light. The light becoming the P-polarized light is transmitted through the polarizing beam splitter 18 and is received by the image acquisition element. In other words, if a normal-dispersion waveplate, which has been conventionally used as a $\lambda/4$ wavelength plate, is used, light that is normally rotated by 90 degrees to become P-polarized light is under rotated or over rotated depending on the wavelength, thus causing the extinction ratio to fluctuate when transmitted through the polarizing beam splitter 18 and thus causing luminance unevenness.

This is not a problem for pickup optical systems or laser targeting devices as long as a suitable wavelength plate for a wavelength band to be used is selected, but it is fatal when observation using a visible wavelength band and a narrow band is performed, as in endoscopes.

A subject image from the objective optical system 16 enters the depolarizing plate 28, and polarized light produced when entering at Brewster's angle is depolarized by the depolarizing plate 28 and is separated in the first prism 18a into a P-component (transmitted light) and an S-component (reflected light) by the polarized-light separating film 18e, which is provided on the beam splitting surface of the first prism 18a. Thus, the subject image is separated into two optical images, i.e., an optical image of the reflected light and an optical image of the transmitted light.

The S-component optical image is reflected at the polarized-light separating film 18e toward the opposite side to the image acquisition element 17, travels in a light path A, is transmitted through the $\lambda/4$ wavelength plate 18d, and is returned at the mirror 18c toward the image acquisition element 17. The returned optical image is again transmitted through the $\lambda/4$ wavelength plate 18d, thus being rotated in its polarized-light direction by 90 degrees, is transmitted through the polarized-light separating film 18e, and is imaged on the image acquisition element 17.

The P-component optical image is transmitted through the polarized-light separating film 18e, travels in a light path B, is reflected at a mirror surface that reflects the image perpendicularly toward the image acquisition element 17 and that is provided at an opposite side of the second prism 18b to the beam splitting surface thereof, and is imaged on the image acquisition element 17. At this time, a prism glass path is set so as to cause a predetermined optical path difference of about several tens of μm, for example, between the light path A and the light path B, and two optical images having different focus positions are imaged on a light-receiving surface of the image acquisition element 17. Accordingly, it is possible to obtain, as a pair of images, a near point image (image A) through the light path A and a far point image (image B) through the light path B.

Specifically, in order to be able to separate the subject image into two optical images having different focus positions, the first prism 18a and the second prism 18b are disposed such that the optical path length on the reflected light side becomes shorter (smaller) than the optical path length (glass path length) on the transmitted light side leading to the image acquisition element 17, in the first prism 18a.

Figure 3:
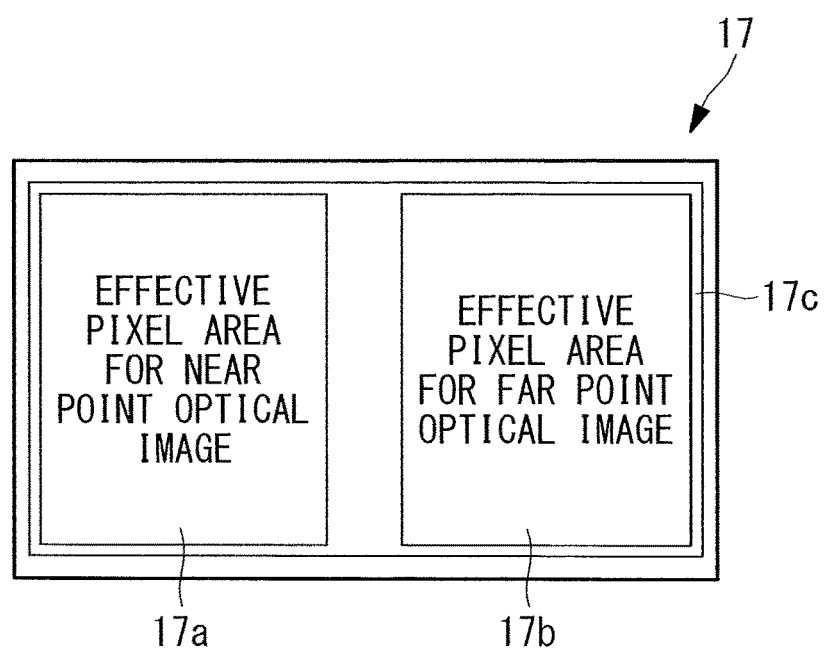
FIG. 3 is a view showing, in outline, the configuration of an image acquisition element used in the endoscope system according to the embodiment of the present invention.

As shown in FIG. 3, in order to acquire two optical images having different focus positions by individually receiving the light beams, the image acquisition element 17 is provided with two light-receiving areas (effective pixel areas) 17a and 17b in the entire pixel area of the image acquisition element 17. In order to acquire two optical images, the light-receiving areas 17a and 17b are arranged so as to correspond with imaging planes of these optical images, respectively. Then, in the image acquisition element 17, the light-receiving area 17a is shifted in focus position toward a near point side relative to the light-receiving area 17b, and the light-receiving area 17b is shifted in focus position toward a far point side relative to the light-receiving area 17a. Accordingly, two optical images having different focus positions are imaged on the light-receiving surface of the image acquisition element 17.

Furthermore, a correction pixel area 17c that is used to correct a geometric shift between the two separated optical images is provided around the light-receiving areas 17a and 17b. Manufacturing errors are corrected in the correction pixel area 17c, and correction is performed through image processing by an image-correction processing unit 32, to be described later, thereby resolving the above-described optical-image geometric shift.

Figure 4A:
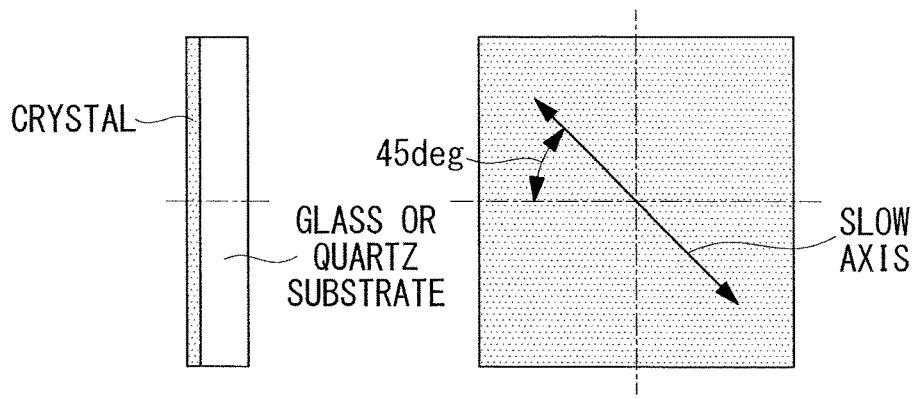
FIG. 4A is a view showing, in outline, the configuration of an example depolarizing plate used in the endoscope system according to the embodiment of the present invention.

Note that a description has been given of an example case in which a $\lambda/4$ wavelength plate is used as the depolarizing plate 28; however, the depolarizing plate is not limited thereto, and a zero-order $\lambda/4$ wavelength plate that is connected to a glass or quartz substrate through bonding or optical contact, shown in FIG. 4A, can be applied thereto. Even with a zero-order $\lambda/4$ wavelength plate, which has too small a thickness to be used by itself, when the zero-order $\lambda/4$ wavelength plate is bonded to a glass substrate or a quartz substrate, a desired strength can be maintained. For example, when a crystal is used for the depolarizing plate 28, the thickness thereof becomes 15 μm, which is very thin, at the design wavelength of 550 nm, thus making handling extremely difficult. Thus, the crystal is bonded to a glass substrate or a quartz substrate, thus maintaining a desired strength and making handling easy.

Figure 4B:
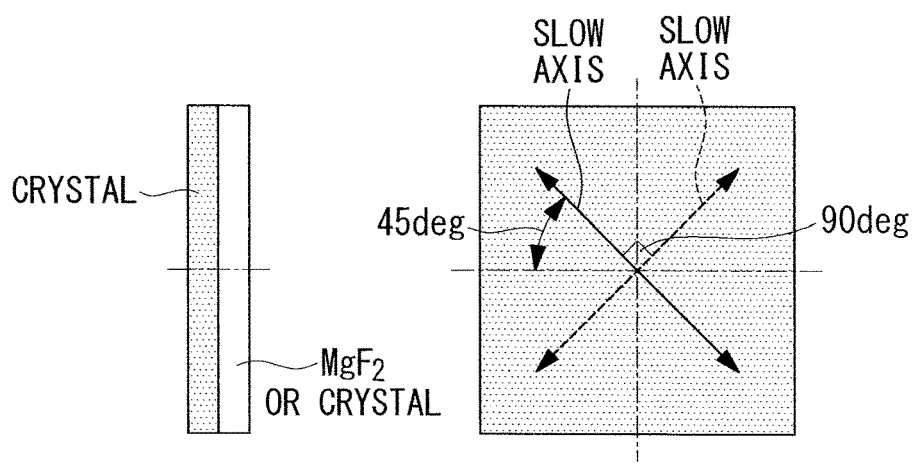
FIG. 4B is a view showing, in outline, the configuration of an example depolarizing plate used in the endoscope system according to the embodiment of the present invention.

Furthermore, as shown in FIG. 4B, it is also possible to use, as the depolarizing plate 28, two inorganic wavelength plates whose optical axes are perpendicular to each other and to configure them such that the thickness t (mm) of at least one of the two inorganic wavelength plates satisfies the following conditional expressions, $$0.135 \leq t \leq 0.3 \quad (1)$$

$$t=(k*0.25\lambda/\Delta n)*10^{-6} \quad (2)$$

$$9 \leq k \leq 19.5 \quad (3)$$

where t (mm) is the thickness of a single inorganic wavelength plate, k is a desired coefficient, λ (nm) is a design center wavelength, and Δn is a difference between a refractive index at ordinary light and a refractive index at extraordinary light.

Although the cost is increased when a zero-order wavelength plate is used, a multiple-order wavelength plate made of the same material is used in this way, thereby making is possible to realize a function substantially equivalent to that of a zero-order wavelength plate, while reducing the cost. Specifically, a depolarizing plate with low angle dependence and high performance can be obtained.

The above-described conditional expressions define the thickness of a single wavelength plate for allowing easy handling and for preventing an increase in the size of the endoscope distal-end portion. Furthermore, when wavelength plates made of the same material are used, the thickness difference Δt therebetween is configured so as to obtain a desired phase difference. When a depolarizing plate formed of two wavelength plates is used, it is preferred that the total thickness of the depolarizing plate fall within the range from 0.3 to 0.6 mm in order to prevent an increase in the size of the endoscope distal-end portion and to be resistant to impacts or stress.

Conceivable specific examples of inorganic wavelength plates include a configuration in which two inorganic wavelength plates are both made of crystal and a configuration in which the two inorganic wavelength plates are made of a combination of different materials, i.e., crystal and $MgF_2$.

Figure 4C:
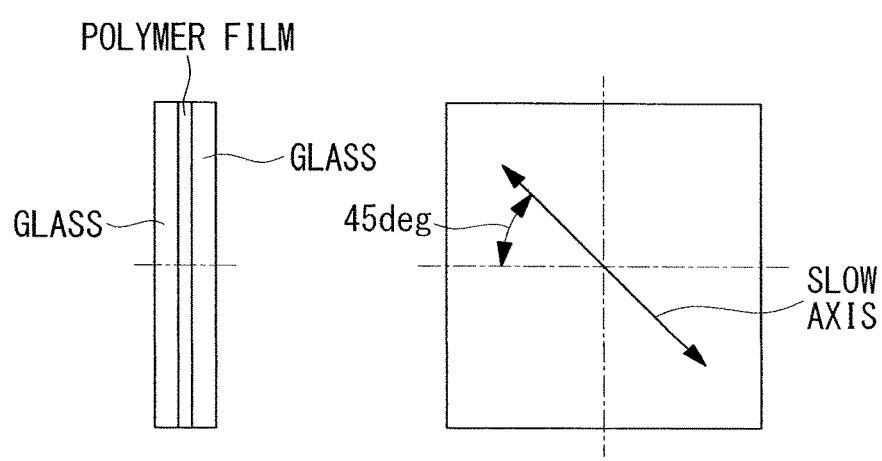
FIG. 4C is a view showing, in outline, the configuration of an example depolarizing plate used in the endoscope system according to the embodiment of the present invention.

Furthermore, as shown in FIG. 4C, the depolarizing plate 28 can be configured by sandwiching a polymer film between glass or quartz substrates.

Figure 5A:
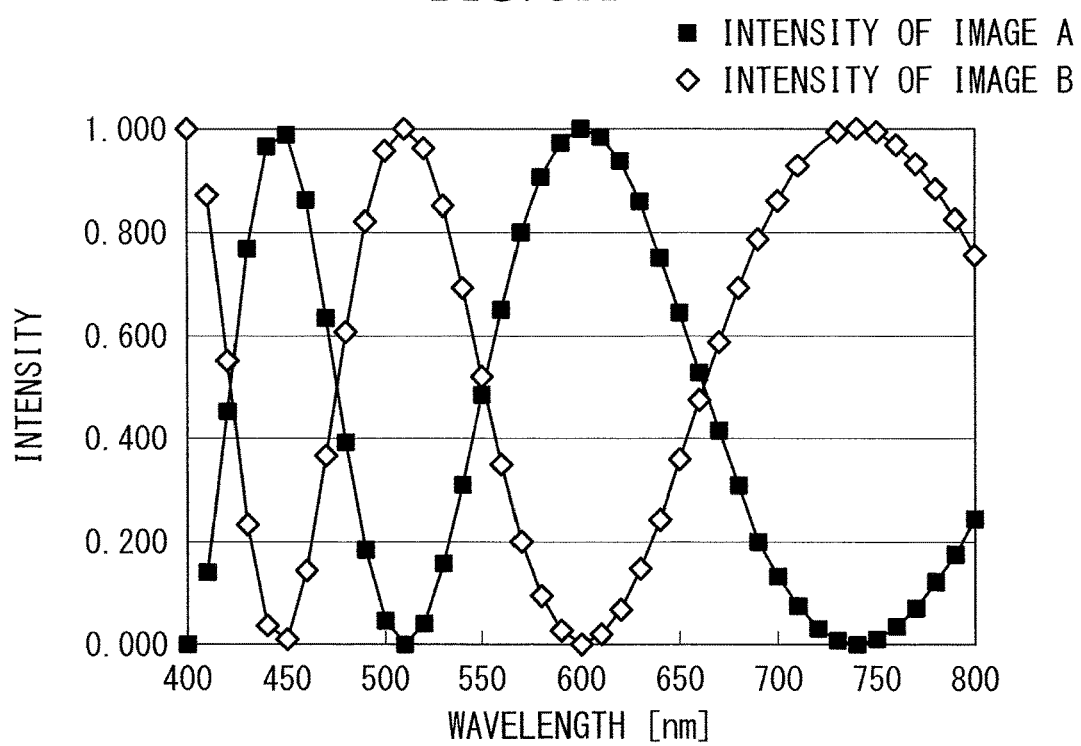
FIG. 5A is a graph showing the relationship between a depolarizing plate and the intensities of a pair of images.
Figure 5B:
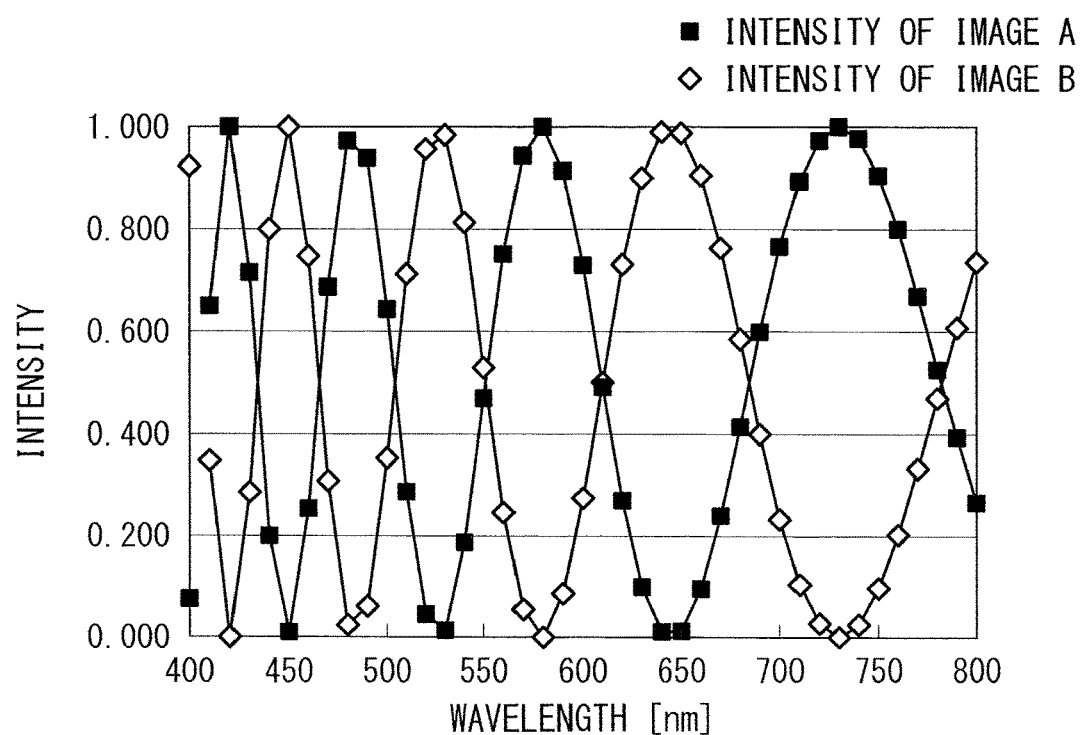
FIG. 5B is a graph showing the relationship between a depolarizing plate and the intensities of the pair of images.

FIG. 5A is a graph showing the intensities of a pair of images when a wavelength plate having a thickness t of 0.15 mm is used as a depolarizing plate. Furthermore, FIG. 5B is a graph showing the intensities of a pair of images when a wavelength plate having a thickness t of 0.27 mm is used as a depolarizing plate.

Figure 6:
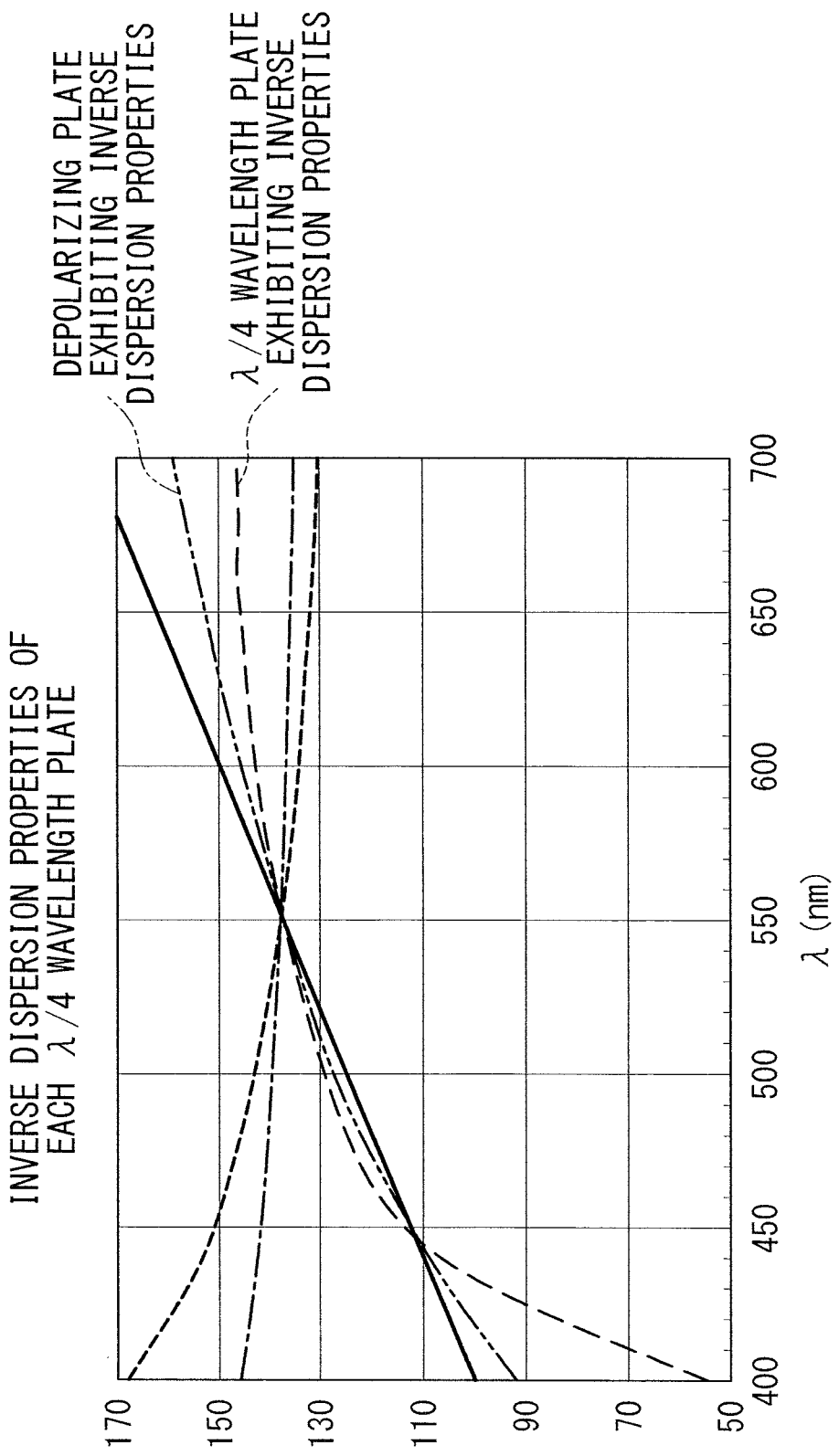
FIG. 6 is a graph showing wavelength dispersion properties when a depolarizing plate and a λ/4 wavelength plate have inverse dispersion properties.

FIG. 6 shows wavelength dispersion properties when the depolarizing plate 28 and the λ/4 wavelength plate 18d have inverse dispersion properties. Note that, in FIG. 6, a two-dot chain line indicates a depolarizing plate using inorganic wavelength plates made of a combination of different materials, and a broken line indicates a λ/4 wavelength plate that is formed of a polymer film.

Figure 7:
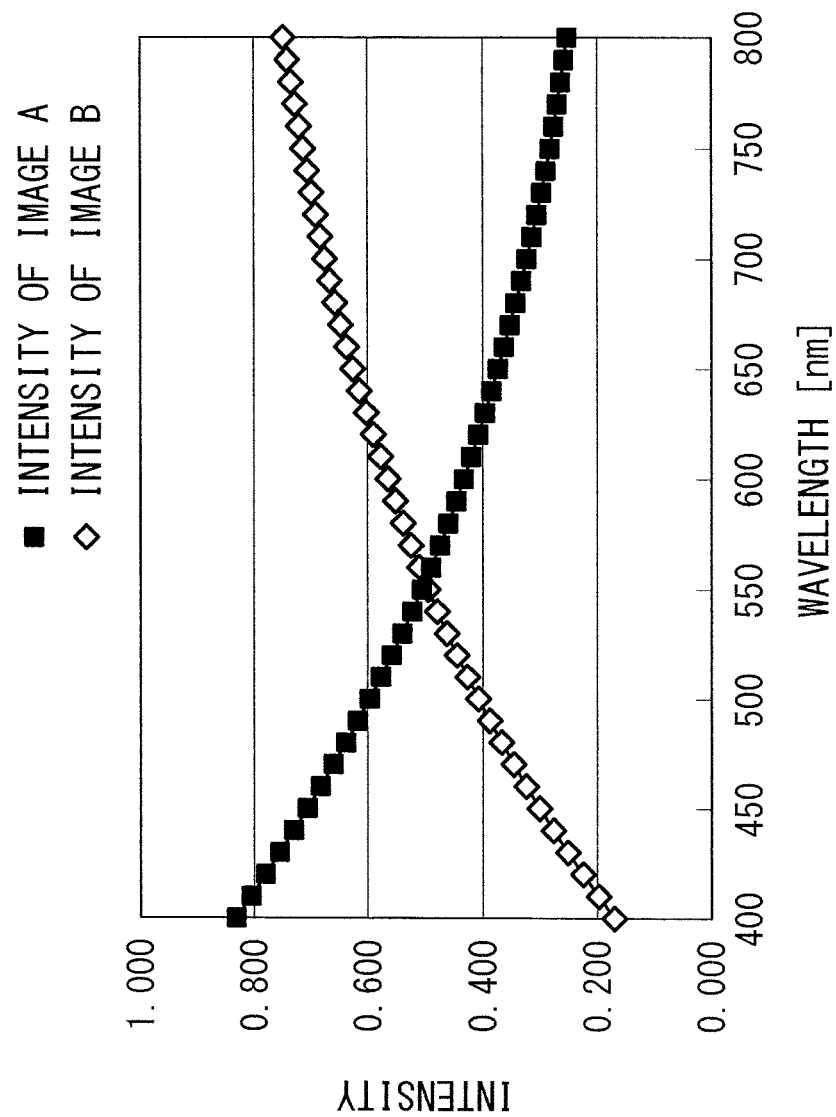
FIG. 7 is an intensity distribution graph of a pair of images when a zero-order wavelength plate that gives a λ/4 phase difference at a wavelength of 550 nm is used.

Furthermore, a polymer film can be used as the λ/4 wavelength plate 18d, and, in this case, it is possible to contribute to a reduction in the size of the endoscope system and to reduce the cost. Furthermore, the above-described λ/4 wavelength plate 18d has inverse dispersion properties; however, the λ/4 wavelength plate 18d need not necessarily have inverse dispersion properties if a zero-order wavelength plate is used as the λ/4 wavelength plate 18d, for example. FIG. 7 shows an intensity distribution graph of a pair of images when a zero-order wavelength plate that gives a λ/4 phase difference at the wavelength of 550 nm is used, for example.

The focus lens 21 can be moved to two positions in the optical axis direction and is driven by the actuator 22 so as to be moved from one position to another position and from the other position to the one position between the two positions. When the focus lens 21 is set at the front-side (object-side) position, a subject located in an observation area used for distant observation is set to be focused on, and when the focus lens 21 is set at the rear-side position, a subject located in an observation area used for close observation is set to be focused on.

Note that the actuator 22 is connected to a signal line 23 inserted through the insertion portion 6, and the signal line 23 is further inserted through a second cable 24 extending from the operating portion 7. A signal connector 24a provided at an end portion of the second cable 24 is detachably connected to the processor device 4, and the signal line 23 is connected to an actuator control unit 25 that is provided in the processor device 4.

The actuator control unit 25 receives, for example, a switching operation signal from a switching operation switch 26 that is provided in the operating portion 7 of the endoscope 2. The actuator control unit 25 applies a driving signal for electrically driving the actuator 22, in response to the operation of the switching operation switch 26, to move the focus lens 21.

Note that the switching operation means for generating a switching operation signal is not limited to the switching operation switch 26 and may be a switching operation lever or the like. The focus lens 21, the actuator 22, and the actuator control unit 25 constitute a focus switching mechanism. Incidentally, a focus means in this application is not limited to the above-described means for moving the focus lens in the optical-axis direction. For example, it is also possible to adopt a means for switching focus by inserting or detaching a lens or a filter into or from the objective optical system.

The image acquisition element 17 is connected to signal lines 27a that is inserted through the insertion portion 6, the operating portion 7, and the second cable 24 and is connected to an image processor 30 that is provided in the processor device 4 and that serves as an image processing unit, when the signal connector 24a is connected to the processor device 4.

The image processor 30 is provided with: an image reading unit 31 that reads respective images of two optical images having different focus positions, acquired by the image acquisition element 17; the image-correction processing unit 32, which performs image correction for the two images read by the image reading unit 31; and the image-compositing processing unit 33, which performs image compositing processing for compositing the two corrected images.

The image-correction processing unit 32 corrects the images of the two optical images, which are imaged on the light-receiving areas 17a and 17b of the image acquisition element 17, such that differences other than the difference in their mutual focus positions become almost the same. Specifically, the two images are corrected such that the relative positions, the angles, and the magnifications in the optical images of the two images become almost the same. Specifically, the image-correction processing unit 32 uses the correction pixel area 17c to perform correction such that the relative position, the angle, and the magnification in the light-receiving area 17a become almost the same as those in the light-receiving area 17b with reference to the light-receiving area 17b, for example.

In a case in which a subject image is separated, and the separated images are individually imaged on the image acquisition element 17, geometric differences therebetween may be caused in some cases. Specifically, the respective optical images imaged on the light-receiving areas 17a and 17b of the image acquisition element 17 may have a relative shift in magnification, shift in position, or shift in angle, i.e., in rotational direction, in some cases. Although it is difficult to completely resolve these differences at the time of manufacturing etc., if the amounts of the shifts are increased, a composited image may become a double image, or an unnatural luminance unevenness etc. may be caused therein. Thus, the image-correction processing unit 32 corrects the above-described geometric differences and luminance difference.

In order to correct the luminance difference between two images, it is preferred that correction be performed with reference to an optical image or image that has a higher luminance of two optical images or images or an optical image or image that has a higher luminance at relatively the same position of the two optical images or images.

In other words, luminance correction is performed so as to conform to a relatively brighter image, i.e., an image having a higher intensity (signal level) of a luminance signal (for example, G signal). If a brighter image is corrected by being multiplied by a negative gain, color saturation noise is likely to occur. In particular, in an image having an area that is saturated by causing halation, there is a problem in that color unevenness is caused in the halation area. This is because RGB sensitivities at the pixels in a sensor are different. In a state of halation or high luminance close thereto, because the state is already saturated even if an attempt to reduce the gain is made, for example, R cannot be corrected, and only gains for G and B are reduced, and, as a result, the halation portion becomes magenta colored.

Figure 8:
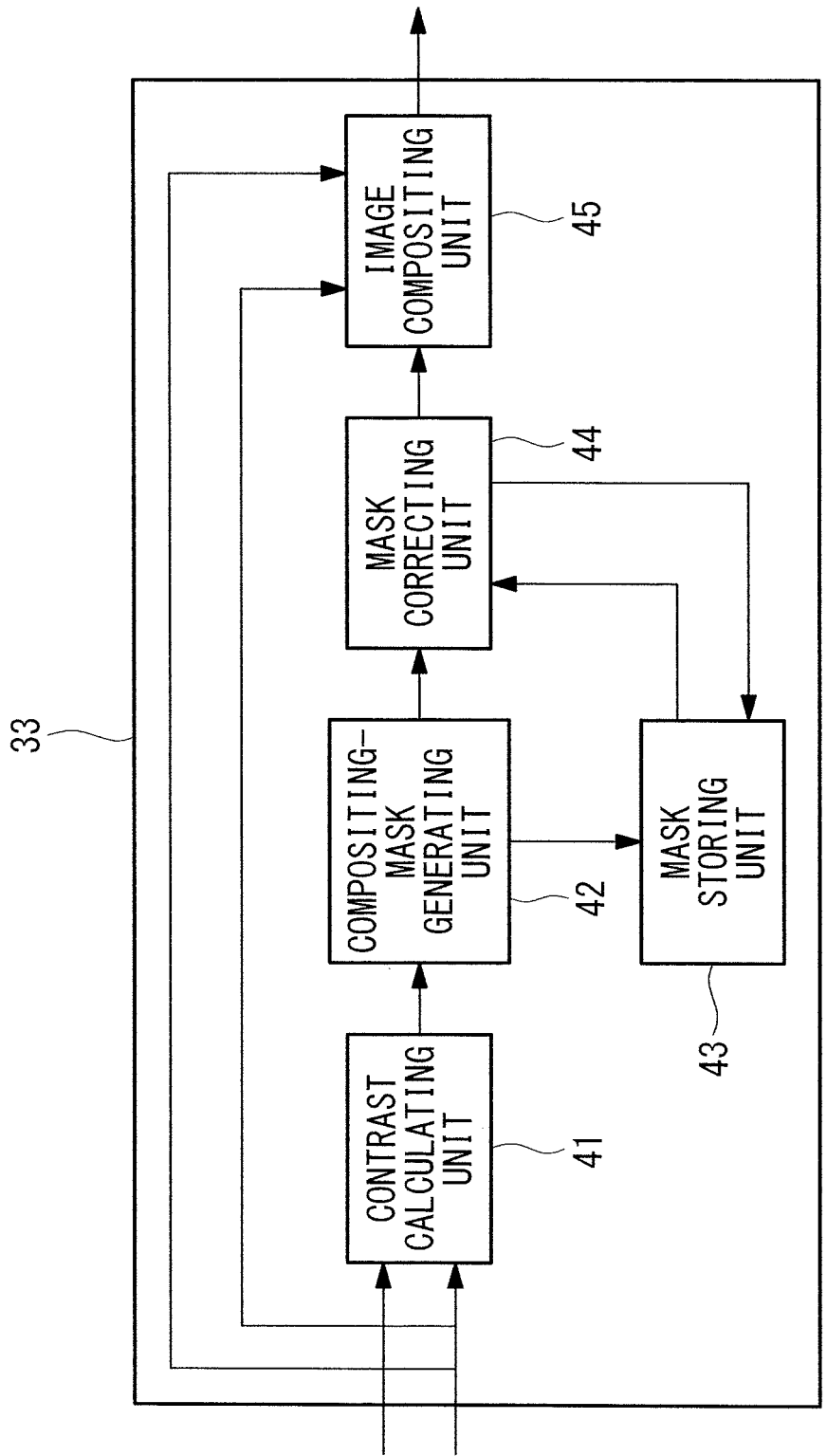
FIG. 8 is a block diagram showing, in outline, the configuration of an image-compositing processing unit in the endoscope system according to the embodiment of the present invention.

The image-compositing processing unit 33 generates a composited image by compositing the corresponding pixels between the pair of images corrected by the image-correction processing unit 32 and is provided with: a contrast calculating unit 41, a compositing-mask generating unit 42, a mask storing unit 43, a mask correcting unit 44, and an image compositing unit 45, as shown in FIG. 8.

The contrast calculating unit 41 calculates the contrast image acquisition element 17 and corrected by the image-correction processing unit 32. In other words, in each of the pair of images, a frequency component is calculated, and the contrast is calculated, from this frequency component, to serve as an evaluation value indicating the degree of in-focus at each pixel. In calculating the frequency component, it is possible to use an existing differential filter, a band-pass filter designed for a subject, or the like.

The compositing-mask generating unit 42 calculates, from the contrasts calculated in the contrast calculating unit 41, contrast ratios, which are the ratios of the contrasts, and generates a compositing mask that serves as the compositing ratios of the corresponding pixels between the pair of images, on the basis of the calculated contrast ratios. The generated compositing mask is stored in the mask storing unit 43. Furthermore, the mask storing unit 43 stores a plurality of compositing masks generated in time series by the compositing-mask generating unit 42 with respect to a plurality of pairs of images acquired in time series by the image acquisition element 17. Note that it is preferred that, when a mask is corrected by the mask correcting unit 44, to be described later, the corrected mask be stored in the mask storing unit 43 instead of the compositing mask.

The mask correcting unit 44 refers to a plurality of compositing masks that have already been generated for the past images and stored in the mask storing unit 43, corrects the compositing mask, and generates a corrected mask. Specifically, the mask correcting unit 44 performs weighting such that the percentage of past compositing masks is higher at pixels that constitute a static area and an area having contrast lower than a predetermined threshold, in the pair of images, than at pixels that constitute a moving-object area or an area having contrast equal to or higher than the predetermined threshold, in the pair of images, and subjects the plurality of compositing masks to weighted averaging, thereby generating a corrected mask. Note that determination of a moving-object area is performed as follows. In other words, as a result of comparing the past masks stored in the mask storing unit 43 with the calculated compositing mask, an area with a large difference is determined as an area with a large change from the past masks, i.e., as a moving-object area.

The image compositing unit 45 generates a composited image by compositing the pair of images according to the corrected mask.

Furthermore, the image processor 30 has: a post image processing unit 34 that subjects the composited image generated by the image-compositing processing unit 33 to post image processing, such as color matrix processing, contour enhancement, and gamma correction; and an image output unit 35 that outputs an image that has been subjected to the post image processing. The image output from the image output unit 35 is output to the image display device 5.

Furthermore, the image processor 30 has a light control unit 36 that generates, from the images read by the image reading unit 31, a light control signal for controlling light to obtain the standard luminance and outputs the light control signal generated by the light control unit 36 to the diaphragm driving unit 14 of the light source device 3. The diaphragm driving unit 14 adjusts, according to the light control signal, the degree of opening of the diaphragm 12 so as to maintain the standard luminance.

Furthermore, in this embodiment, a correction-parameter storing unit 37 that stores (information of) correction parameters that are used to correct images in the image-correction processing unit 32 is provided.

Here, a correction parameter is determined in consideration of the properties of an optical-path dividing element, an image acquisition element, and a λ/4 plate. For example, depending on the shading properties of an optical-path dividing element and an image acquisition element and the wavelength characteristics of a λ/4 wavelength plate, the above-described geometric differences and luminance difference or a color difference may be caused in the images of the two optical images.

Furthermore, when the wavelength band of illumination light produced in the light source device is selectively switched, for example, when the endoscope system has a plurality of observation modes, such as a normal observation mode, a narrow-band observation mode, etc., and uses a different wavelength band of illumination light depending on the observation mode, a luminance difference may also be caused between the two images. If there is a luminance difference between the two images, unnatural luminance unevenness or color unevenness is caused in a composited image.

Thus, for example, in consideration of the properties of the optical-path dividing element, the image acquisition element, and the λ/4 plate, luminance correction parameters corresponding to the observation modes, i.e., corresponding to the wavelength bands of illumination light, are stored in the correction-parameter storing unit 37 as IDs for the respective observation modes. A control unit 39 switches the correction parameter corresponding to the observation mode, and the image-correction processing unit 32 performs image correction on the basis of the selected correction parameter.

More specifically, for example, when the wavelength dependence of a ¼λ wavelength plate or a depolarizing plate is large (when an achromat is not used), or when the polarized-light separating film of the polarizing beam splitter has large wavelength dependence, the luminance correction value does not necessarily become optimum depending on the wavelength band of illumination light for observing a subject, thus causing luminance unevenness, in some cases.

Figure 9:
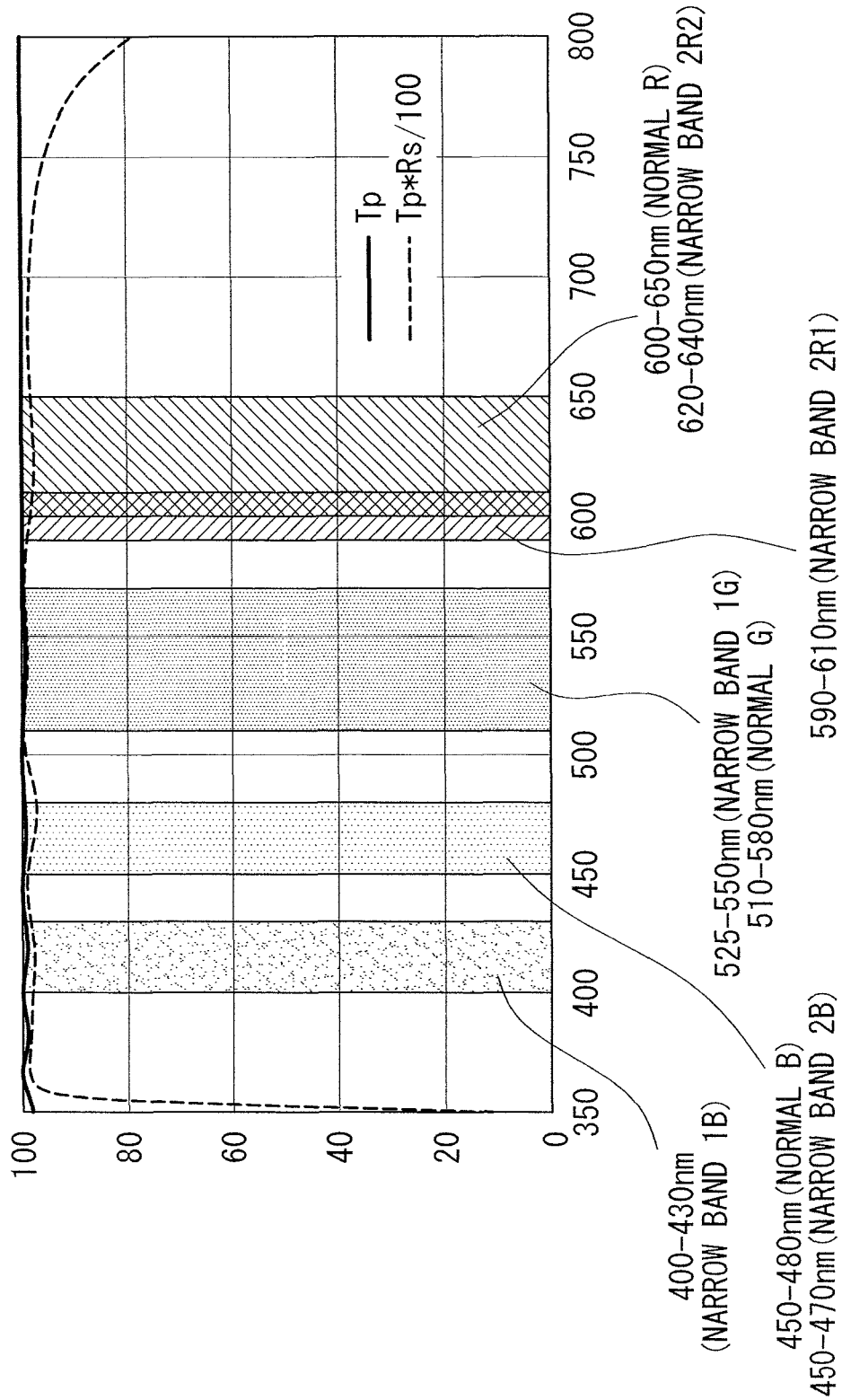
FIG. 9 is a graph of the spectral characteristics of a polarization separation coating used for a polarizing beam splitter, showing the spectral characteristics on the optical axis.
Figure 10:
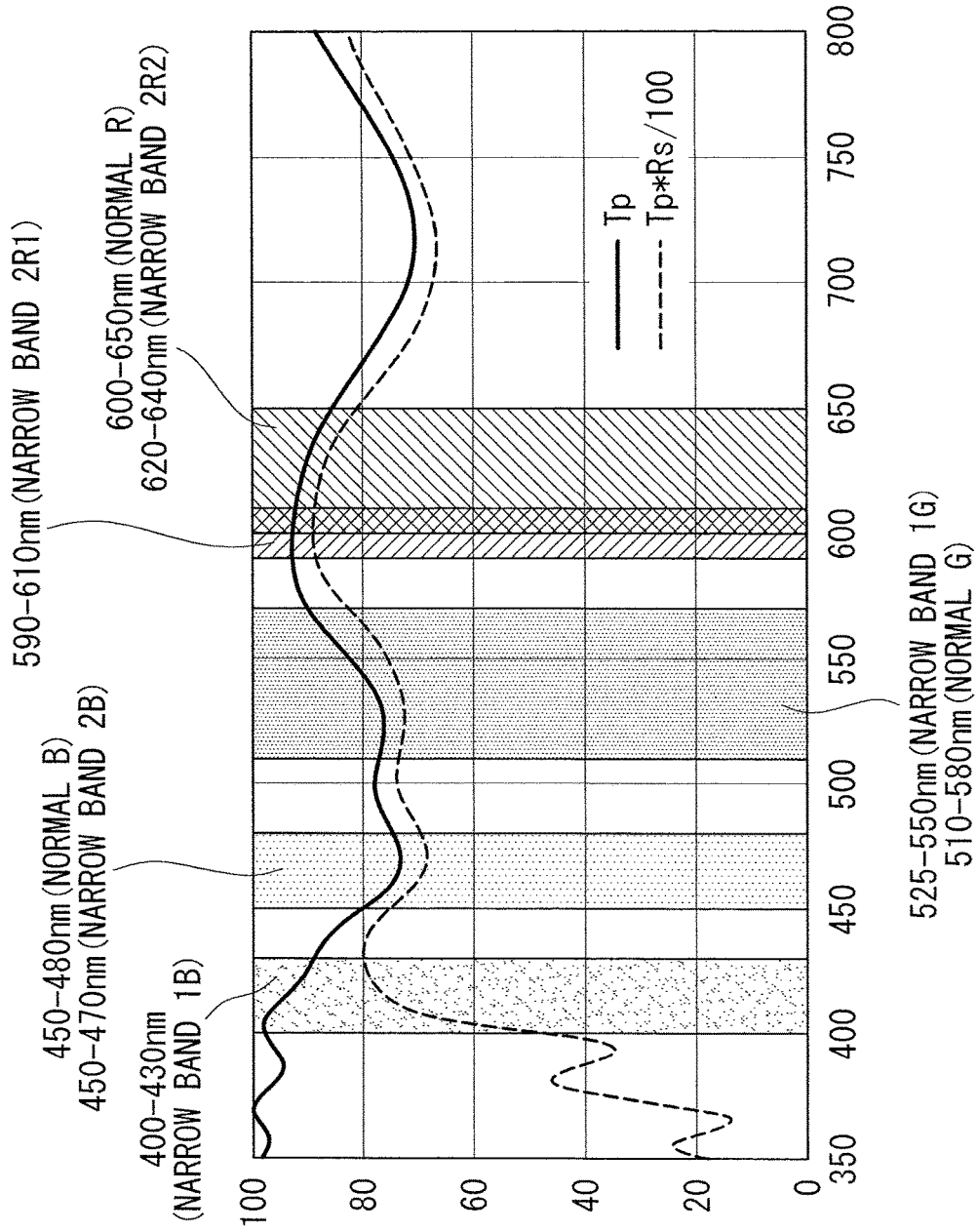
FIG. 10 is a graph of the spectral characteristics of a polarization separation coating used for the polarizing beam splitter, showing the spectral characteristics obtained when a light beam inclined at an angle of −7 degrees with respect to the optical axis is incident on the polarization separation coating.
Figure 11:
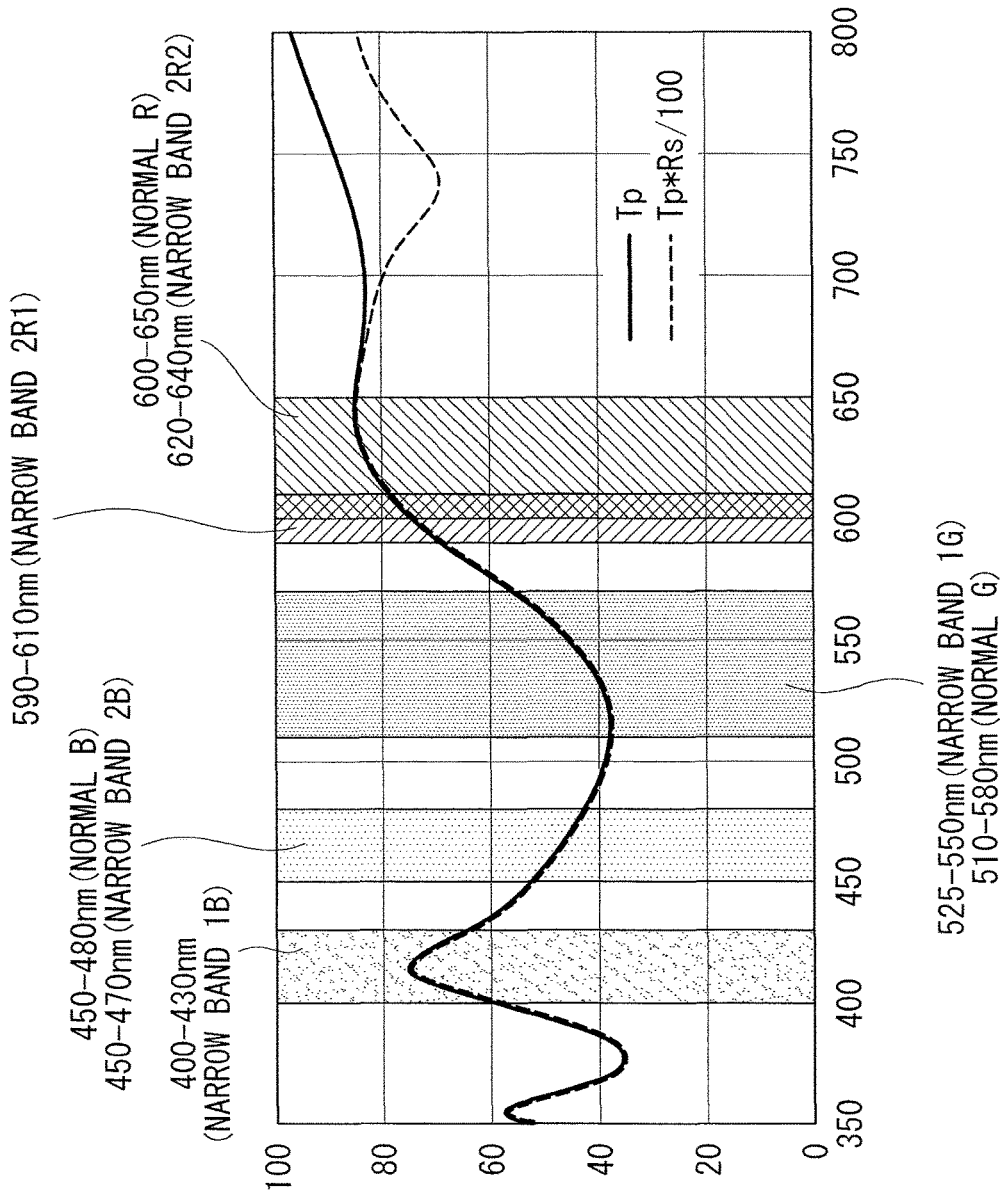
FIG. 11 is a graph of the spectral characteristics of a polarization separation coating used for the polarizing beam splitter, showing the spectral characteristics obtained when a light beam inclined at an angle of +7 degrees with respect to the optical axis is incident on the polarization separation coating.

FIGS. 9 to 11 are graphs showing the spectral characteristics of a polarization separation coating used for the polarizing beam splitter. In each figure, a solid line indicates a spectral graph (Tp) of the far-point light path, and a broken line indicates a spectral graph (Tp*Rs/100) of the near-point light path.

FIG. 9 shows the spectral characteristics of a light beam entering, at an angle of 0 degrees, the polarizing-beam-splitter surface, which is inclined at an angle of 45 degrees with respect to the optical axis, i.e., shows the spectral characteristics on the optical axis. FIG. 10 shows the spectral characteristics when a light beam inclined at an angle of −7 degrees with respect to the optical axis enters the polarization separation coating. FIG. 11 shows the spectral characteristics when a light beam inclined at an angle of +7 degrees enters the polarization separation coating. Note that the sign of the angle is positive in the clockwise direction.

A description will be given below of an example case in which a light source using a frame sequential method is used as the light source device 3 of this embodiment, and there are three observation modes, i.e., a normal observation mode, a narrow-band observation mode 1, and a narrow-band observation mode 2. In this case, as wavelength bands used for RGB in the normal observation mode, a wavelength band from 600 to 650 nm is used for R, a wavelength band from 510 to 580 nm is used for G, and a wavelength band from 450 to 480 nm is used for B. On the other hand, in the narrow-band observation mode 1, which mainly uses a short wavelength side, a wavelength band from 525 to 550 nm is used for G, and a wavelength band from 400 to 430 nm is used for B.

As shown in FIGS. 10 and 11, it is understood that there is a large difference, in particular, in the intensity of B in each of the oblique-incidence observation modes. In other words, if the same correction parameter is used for images acquired in the normal observation mode and images acquired in the narrow-band observation mode 1, luminance unevenness is caused in the images acquired in the narrow-band observation mode 1. Therefore, it is necessary to apply correction parameters corresponding to the respective observation modes by making a luminance-correction parameter for images acquired in the normal observation mode different from a luminance-correction parameter for images acquired in the narrow-band observation mode 1.

Thus, the correction parameter is switched between the case where the wavelength band from 450 to 480 nm for B is used in the normal observation mode and the case where the wavelength band from 400 to 430 nm for B is used in the narrow-band observation mode 1.

Furthermore, in the narrow-band observation mode 2, a wavelength band from 590 to 610 nm is used for R1, a wavelength band from 620 to 640 nm is used for R2, and a wavelength band from 450 to 470 nm is used for B.

Specifically, the narrow-band observation mode 2 is an observation mode in which a wavelength band from 510 nm to 580 nm is not used.

In this case, in the normal observation mode, a correction parameter that is determined in consideration of a wavelength band from 525 to 550 nm for G, too, is used; thus, when the observation mode is switched from the normal observation mode to the narrow-band observation mode 2, a gap in luminance correction parameter is caused, thus causing luminance unevenness.

Thus, when the wavelength band from 525 to 550 nm for G, which is not used in the narrow-band observation mode 2 and is used in the normal observation mode, is used, the correction parameter is switched.

Switching of the correction parameter can be interlocked with switching of the observation mode, i.e., can be interlocked with an observation-mode switch SW on an endoscope body, a foot SW (not shown), or the like.

For example, when the observation-mode switch SW is pressed to switch the observation mode, a filter is switched in the light source device on receiving a switch signal, thereby radiating light having a wavelength band corresponding to the selected observation mode. Then, in conjunction with switching of the observation mode, a correction parameter corresponding to the selected observation mode is read from the correction-parameter storing unit 37, and the optimum correction processing is performed in the image-correction processing unit 32. Note that, if the light source is an LED light source, it is possible to switch to an LED corresponding to the selected observation mode, and the parameter may be switched in conjunction therewith.

Figure 12:
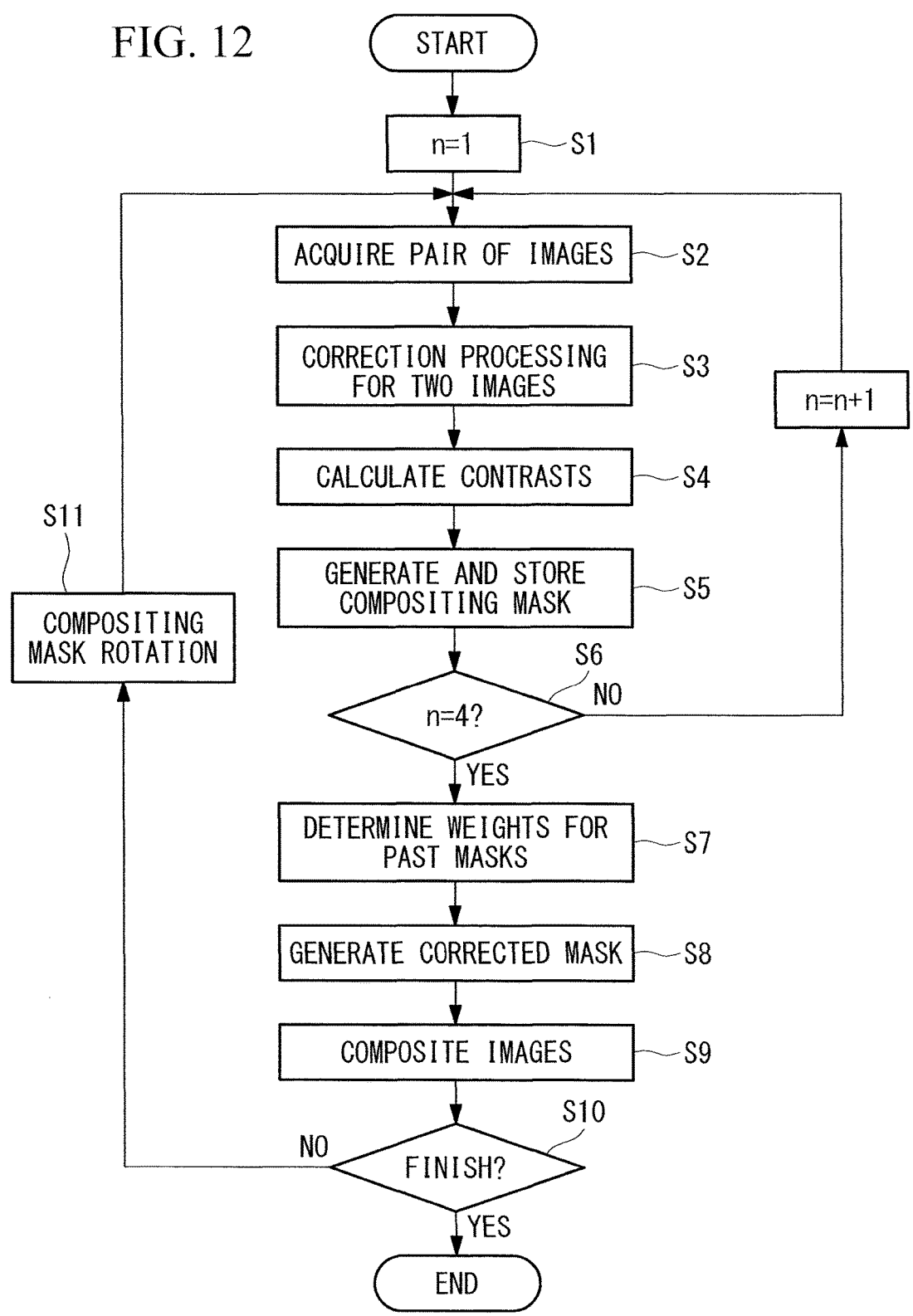
FIG. 12 is a flowchart showing the flow of compositing two images in the endoscope system according to the embodiment of the present invention.

Next, the flow of compositing a pair of optical images in this embodiment will be described with reference to a flowchart shown in FIG. 12. Note that a description will be given below of an example case in which three past compositing masks are used when a compositing mask is corrected.

In Step S1, counting is started to count the number of times that a past mask required for compositing-mask correction is generated. In Step S2, the image acquisition element 17 acquires, for one subject, the far point image of a far-point optical image and the near point image of a near-point optical image that have different focus positions. In Step S3, the image-correction processing unit 32 subjects the far point image and the near point image, which are acquired in Step S2, to correction processing. Specifically, the two images are corrected, according to a correction parameter set in advance, such that the relative positions, the angles, and the magnifications in the images become almost the same, and the corrected images are output to the image-compositing processing unit 33. Note that the two images may be subjected to correction in terms of luminance or color difference as needed.

In Step S4, the contrast calculating unit 41 of the image-compositing processing unit 33 calculates the contrast values of the pixels of the two images that have been subjected to correction processing. The calculated contrast values are output to the compositing-mask generating unit 42. In Step S5, from the contrasts calculated in the contrast calculating unit 41, the contrast ratios, which are the ratios of the contrasts, are calculated. A compositing mask that serves as compositing ratios of corresponding pixels between the pair of images is generated on the basis of the calculated contrast ratios and is stored in the mask storing unit 43.

In Step S6, it is determined whether processing including: acquisition of a pair of images in the image acquisition element 17; the predetermined correction processing; calculation of the contrasts; and generation and storing of the compositing mask has been performed four times. If the processing has not been performed four times, the flow returns to Step S2. If the processing has been performed four times, the flow advances to Step S7.

Figure 13:
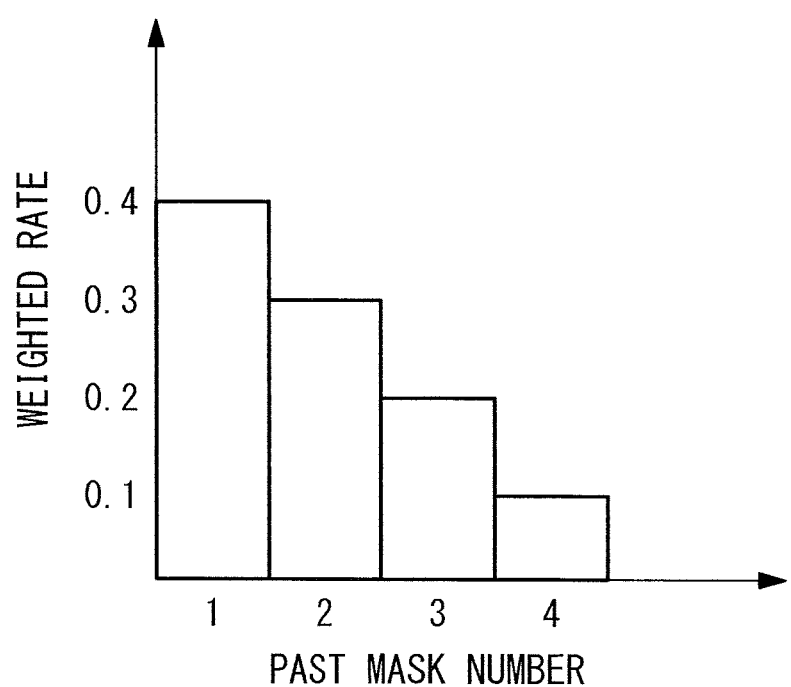
FIG. 13 is a graph showing example weighting performed in a case in which past compositing masks are subjected to weighted averaging, in the endoscope system according to the embodiment of the present invention.

In Step S7, the mask correcting unit 44 determines weights such that the percentage of the past compositing masks is higher at pixels that constitute a static area and an area having contrast lower than a predetermined threshold, in the pair of images, than at pixels that constitute a moving-object area and an area having contrast equal to or higher than the predetermined threshold, in the pair of images. Here, the weights can be sequentially calculated according to a predetermined conditional expression, for example, or can be determined in advance, as shown in FIG. 13.

Figure 14:
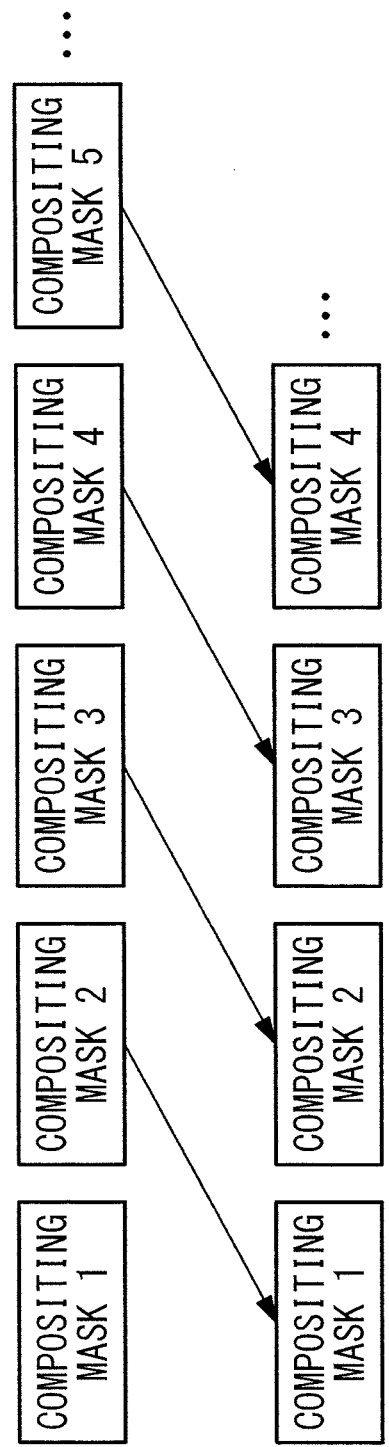
FIG. 14 is a view for explaining a case in which past compositing masks to be subjected to weighted averaging are sequentially changed in time series, in the endoscope system according to the embodiment of the present invention.

In Step S8, a corrected mask is generated by correcting the compositing mask according to the weights determined in Step S7 and is output to the image compositing unit 45. In Step S9, a composited image is generated by compositing the pair of images including the far point image and the near point image according to the corrected mask. In Step S10, it is determined whether the image compositing processing has been finished. If the image compositing processing has not been finished, in Step S11, the counting numbers of compositing masks stored in the mask storing unit 43 are sequentially shifted (see FIG. 14), n is set to 4, and processing from Step S2 to Step S5 is performed.

Note that a description has been given above of an example case in which four compositing masks are subjected to weighted averaging; however, the present invention is not limited thereto, and the number of masks to be subjected to weighted averaging and the weights thereof can be determined as appropriate.

In this way, according to this embodiment, it is possible to acquire an image in which the depth of field is extended while suppressing luminance unevenness caused by spectral intensity, by preventing a discontinuous area from being caused in a composited image due to noise etc. and further by optimizing the depolarizing plate and the $\lambda/4$ wavelength plate. Furthermore, in consideration of a case in which the compositing mask varies over time, e.g., a case in which a moving-object area is included in the image, a plurality of compositing masks generated in time series are subjected to weighted averaging to generate a corrected mask; therefore, it is possible to prevent a fluctuation in the compositing ratios applied to each frame, in particular, in a low contrast area etc, when images are acquired in time series as in a moving image. Specifically, it is possible to prevent the occurrence of flickering or luminance unevenness that would be caused by switching, for each frame, between an image to which the pixels of a far point image are applied and an image to which the pixels of a near point image are applied, despite the pixel positions being the same.

The above-described embodiment leads to the following inventions.

According to one aspect, the present invention provides an endoscope system including: an objective optical system that is provided at a distal end of an insertion portion and that obtains a subject image of a subject irradiated with illumination light from a light source; an optical-path dividing means that divides the subject image into two optical images having different focus positions; an image acquisition element that simultaneously images the two optical images having different focus positions to acquire a pair of images; a contrast calculating means that calculates contrasts, for respective pixels, of the pair of images acquired by the image acquisition element; a mask generating means that generates a compositing mask that serves as compositing ratios of the corresponding pixels between the pair of images on the basis of the ratios of the contrasts calculated by the contrast calculating means; a mask correcting means that generates a corrected mask by applying, for the respective pixels, weighted averaging to a plurality of compositing masks that are generated in time series by the mask generating means for a plurality of pairs of images that are acquired in time series by the image acquisition element; and an image compositing means that composites the two images according to the corrected mask generated by the mask correcting means, wherein the mask correcting means applies weighted averaging to the plurality of compositing masks by performing weighting such that the percentage of the past compositing masks is higher at pixels that constitute a static area and an area having contrast lower than a predetermined threshold, in the pair of images, than at pixels that constitute a moving-object area or an area having contrast equal to or higher than the predetermined threshold, in the pair of images.

According to the above-described aspect, when a composited image is generated from a pair of images that are acquired by simultaneously imaging two optical images having different focus positions, the contrast calculating means calculates the contrasts for respective pixels of the pair of images. Here, the contrast is used as an evaluation value indicating whether a certain pixel is in focus, and if the contrast is higher, it can be determined that the pixel is in focus. Thus, by calculating the contrasts of the pair of images, it can be determined that a pixel in question is in focus at a far point, at a near point, or at an intermediate point.

Therefore, in the compositing mask generated by the mask generating means on the basis of the ratios of the contrasts for the respective pixels, the compositing ratio is set higher at a pixel having higher contrast of the corresponding pixels between the pair of images.

In this case, in consideration of a case in which the compositing mask varies over time, e.g., a case in which a moving-object area is included in the image, the mask correcting means subjects a plurality of compositing masks generated in time series by the mask generating means to weighted averaging, thus generating a corrected mask. Specifically, the mask correcting means generates a corrected mask in which the percentage of the relatively new past compositing masks is higher for a static area and an area having contrast lower than a predetermined threshold and existing in the pair of images than for a moving-object area or an area having contrast equal to or higher than the predetermined threshold and existing in the pair of images.

By doing so, in a case in which images are acquired in time series as in a moving image, in particular, in a low contrast area etc., the compositing ratios applied to each frame can be prevented from being fluctuated. Specifically, it is possible to prevent the occurrence of flickering or luminance unevenness caused by switching, for each frame, between an image to which the pixels of a far point image are applied and an image to which the pixels of a near point image are applied, despite the pixel positions being the same.

In the above-described aspect, it is preferred to further include: a depolarizing plate that is formed of at least one wavelength plate disposed between the objective optical system and the optical-path dividing means; and a $\lambda/4$ wavelength plate and a reflective mirror that are disposed in the light path of one optical image of the two optical images.

By doing so, polarized light produced when entering at Brewster's angle can be depolarized by the depolarizing plate, and the phase of the light can be rotated by making the light pass through the optical-path dividing means.

In the above-described aspect, it is preferred that the λ/4 wavelength plate have inverse dispersion properties.

By doing so, it is possible to prevent the occurrence of unevenness caused by the difference in intensity at the observation wavelength.

In the above-described aspect, it is preferred that the λ/4 wavelength plate be a polymer film.

By doing so, it is possible to contribute to a reduction in the size of the endoscope system and to reduce the cost.

In the above-described aspect, it is preferred that the λ/4 wavelength plate be a single zero-order wavelength plate.

By doing so, it is possible to obtain a depolarizing plate with low angle dependence and high performance and to contribute to a reduction in the size of the endoscope system.

In the above-described aspect, it is preferred that the depolarizing plate be a zero-order λ/4 wavelength plate that is connected to a glass or quartz substrate through bonding or optical contact.

By doing so, it is possible to obtain a depolarizing plate with low angle dependence and high performance and to contribute to a reduction in the size of the endoscope system.

In the above-described aspect, it is preferred that the depolarizing plate be formed of two inorganic wavelength plates whose optical axes are perpendicular to each other, and the thickness t (mm) of at least one of the two inorganic wavelength plates satisfy the following conditional expressions, $$0.135 \leq t \leq 0.3 \quad (1)$$

$$t = (k*0.25\lambda/\Delta n)*10^{-6} \quad (2)$$

$$9 \leq k \leq 19.5 \quad (3)$$

where t (mm) is the thickness of a single inorganic wavelength plate, k is a desired coefficient, λ (nm) is a design center wavelength, and Δn is a difference between a refractive index at ordinary light and a refractive index at extraordinary light.

By doing so, it is possible to obtain a depolarizing plate with low angle dependence and high performance while reducing the cost.

In the above-described aspect, it is preferred that refractive indexes of the two inorganic wavelength plates be different from each other.

By doing so, it is possible to convert polarized light corresponding to linear polarized light into circularly polarized light, in consideration of wavelength dependent properties.

In the above-described aspect, it is preferred that the depolarizing plate be a polymer film that is sandwiched between glass or quartz substrates.

By doing so, angle dependence can be reduced, and polarized light can be easily depolarized.

It is preferred to further include an image correcting means that corrects a luminance difference between the pair of images on the basis of a predetermined correction parameter, wherein the light source selectively switches between illumination light having wavelength bands different from each other to radiate illumination light having the selected wavelength band onto the subject; and, when the image acquisition element acquires a pair of images based on a subject image of the subject irradiated with illumination light having the selected wavelength band, the correction parameter is switched according to the wavelength band of the illumination light when the image correcting means performs correction.

By doing so, even when a luminance difference is caused between a pair of images by the wavelength band of illumination light produced by the light source, correction is performed according to the wavelength band of illumination light, thereby making it possible to suppress the occurrence of unnatural luminance unevenness or color unevenness in a composited image.

The light source may selectively switch between illumination light that includes a wavelength band from 400 to 430 nm and illumination light that includes a wavelength band from 450 to 480 nm and may radiate the selected illumination light.

Furthermore, the light source may selectively switch to illumination light that does not include a wavelength band from 510 to 580 nm.

By doing so, correction according to the wavelength band is performed for images based on illumination light including a wavelength band that tends to cause luminance unevenness, thereby making it possible to suppress unnatural luminance unevenness or color unevenness.

REFERENCE SIGNS LIST 1 endoscope system
2 endoscope
3 light source device
4 processor device
5 image display device
6 insertion portion
16 objective optical system
17 image acquisition element
17a, 17b light-receiving areas
17c correction pixel area
18 polarizing beam splitter
18a first prism
18b second prism
18c mirror
18d λ/4 wavelength plate
18e polarized-light separating film
19 image acquisition unit
28 depolarizing plate
30 image processor
32 image-correction processing unit
33 image-compositing processing unit
41 contrast calculating unit
42 compositing-mask generating unit
43 mask storing unit
44 mask correcting unit
45 image compositing unit

The invention claimed is:

1. An endoscope system comprising:
    an objective optical system that is provided at a distal end of an insertion portion and that obtains a subject image of a subject irradiated with illumination light from a light source;
    an optical-path dividing portion that divides the subject image into two optical images having different focus positions;
    an image acquisition element that simultaneously images the two optical images having different focus positions to acquire a pair of images;
    a contrast calculating portion that calculates contrasts, for respective pixels, of the pair of images acquired by the image acquisition element;

a mask generating portion that generates a compositing mask that serves as compositing ratios of the corresponding pixels between the pair of images on the basis of the ratios of the contrasts calculated by the contrast calculating portion;

a mask correcting portion that generates a corrected mask by applying, for the respective pixels, weighted averaging to a plurality of compositing masks that are generated in time series by the mask generating portion for a plurality of pairs of images that are acquired in time series by the image acquisition element; and an image compositing portion that composites the two images according to the corrected mask generated by the mask correcting portion, wherein the mask correcting portion applies weighted averaging to the plurality of compositing masks by performing weighting such that the percentage of the past compositing masks is higher at pixels that constitute a static area and an area having contrast lower than a predetermined threshold, in the pair of images, than at pixels that constitute a moving-object area or an area having contrast equal to or higher than the predetermined threshold, in the pair of images.

2. An endoscope system according to claim 1, further comprising:

a depolarizing plate that is formed of at least one wavelength plate disposed between the objective optical system and the optical-path dividing portion; and a λ/4 wavelength plate and a reflective mirror that are disposed in the light path of one optical image of the two optical images.

3. An endoscope system according to claim 2, wherein the λ/4 wavelength plate has inverse dispersion properties.

4. An endoscope system according to claim 3, wherein the λ/4 wavelength plate is a polymer film.

5. An endoscope system according to claim 2, wherein the λ/4 wavelength plate is a single zero-order wavelength plate.

6. An endoscope system according to claim 2, wherein the depolarizing plate is a zero-order λ/4 wavelength plate that is connected to a glass or quartz substrate through bonding or optical contact.

7. An endoscope system according to claim 2, wherein the depolarizing plate is formed of two inorganic wavelength plates whose optical axes are perpendicular to each other, and the thickness t (mm) of at least one of the two inorganic wavelength plates satisfies the following conditional expressions, $$0.135 \leq t \leq 0.3 \quad (1)$$

$$t = (k*0.25\lambda/\Delta n)*10^{-6} \quad (2)$$

$$9 \leq k \leq 19.5 \quad (3)$$

where t (mm) is the thickness of a single inorganic wavelength plate, k is a desired coefficient, λ (nm) is a design center wavelength, and Δn is a difference between a refractive index at ordinary light and a refractive index at extraordinary light.

8. An endoscope system according to claim 7, wherein refractive indexes of the two inorganic wavelength plates are different from each other.

9. An endoscope system according to claim 2, wherein the depolarizing plate is a polymer film that is sandwiched between glass or quartz substrates.

10. An endoscope system according to claim 1, further comprising an image correcting portion that corrects a luminance difference between the pair of images on the basis of a predetermined correction parameter, wherein the light source selectively switches between illumination light having wavelength bands different from each other to radiate illumination light having the selected wavelength band onto the subject; and when the image acquisition element acquires a pair of images based on a subject image of the subject irradiated with illumination light having the selected wavelength band, the correction parameter is switched according to the wavelength band of the illumination light when the image correcting portion performs correction.

11. An endoscope system according to claim 10, wherein the light source selectively switches between illumination light that includes a wavelength band from 400 to 430 nm and illumination light that includes a wavelength band from 450 to 480 nm and radiates the selected illumination light.

12. An endoscope system according to claim 10, wherein the light source selectively switches to illumination light that does not include a wavelength band from 510 to 580 nm.

* * * * *